(12) United States Patent
Cummings

(10) Patent No.: US 10,583,371 B2
(45) Date of Patent: *Mar. 10, 2020

(54) APATITE IN-SITU RESTORATION

(71) Applicant: Bio-Rad Laboratories, Inc., Hercules, CA (US)

(72) Inventor: Larry Cummings, Pleasant Hill, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,816

(22) Filed: Aug. 10, 2018

(65) Prior Publication Data

US 2018/0345174 A1 Dec. 6, 2018

Related U.S. Application Data

(63) Continuation of application No. 14/747,162, filed on Jun. 23, 2015, now Pat. No. 10,092,857.

(60) Provisional application No. 62/082,017, filed on Nov. 19, 2014, provisional application No. 62/015,894, filed on Jun. 23, 2014.

(51) Int. Cl.
| | |
|---|---|
| *B01D 15/20* | (2006.01) |
| *B01D 15/36* | (2006.01) |
| *G01N 30/26* | (2006.01) |
| *B01J 20/281* | (2006.01) |
| *G01N 30/50* | (2006.01) |
| *B01D 15/38* | (2006.01) |
| *C01B 25/32* | (2006.01) |
| *C01B 25/455* | (2006.01) |
| *B01J 20/34* | (2006.01) |
| *B01J 20/282* | (2006.01) |

(Continued)

(52) U.S. Cl.
CPC ......... *B01D 15/203* (2013.01); *B01D 15/361* (2013.01); *B01D 15/3847* (2013.01); *B01J 20/282* (2013.01); *B01J 20/3433* (2013.01); *B01J 20/3475* (2013.01); *C01B 25/32* (2013.01); *C01B 25/327* (2013.01); *C01B 25/455* (2013.01); *G01N 30/26* (2013.01); *G01N 30/48* (2013.01); *G01N 30/50* (2013.01); *B01J 20/048* (2013.01); *B01J 20/3085* (2013.01); *B01J 20/34* (2013.01)

(58) Field of Classification Search
None
See application file for complete search history.

(56) References Cited

U.S. PATENT DOCUMENTS

| | | | |
|---|---|---|---|
| 3,737,516 A | 6/1973 | Jenner | |
| 4,053,561 A | 10/1977 | Irani | |

(Continued)

FOREIGN PATENT DOCUMENTS

| | | |
|---|---|---|
| EP | 0256836 A1 | 2/1988 |
| EP | 1081221 A1 | 3/2001 |

(Continued)

OTHER PUBLICATIONS

U.S. Appl. No. 13/006,022, filed Jan. 13, 2011, Issued.

(Continued)

*Primary Examiner* — Kara M Peo
(74) *Attorney, Agent, or Firm* — Kilpatrick Townsend & Stockton LLP

(57) ABSTRACT

The present invention discloses methods of regenerating apatite surfaces, for example after purification of a target analyte.

19 Claims, 5 Drawing Sheets

(51) Int. Cl.
*B01J 20/04* (2006.01)
*B01J 20/30* (2006.01)

(56) References Cited

U.S. PATENT DOCUMENTS

| | | | |
|---|---|---|---|
| 4,859,342 | A | 8/1989 | Shirasawa et al. |
| 5,332,503 | A | 7/1994 | Lee et al. |
| 5,744,587 | A | 4/1998 | Alaska et al. |
| 5,783,217 | A | 7/1998 | Lee et al. |
| 6,156,178 | A | 12/2000 | Mansfield et al. |
| 6,602,697 | B1 | 8/2003 | Cook, III |
| 7,122,641 | B2 | 10/2006 | Vedantham et al. |
| 7,476,722 | B2 | 1/2009 | Vedantham et al. |
| 7,659,373 | B2 | 2/2010 | Burg et al. |
| 7,767,447 | B2 | 8/2010 | Breidenthal et al. |
| 8,058,407 | B2 | 11/2011 | Sun et al. |
| 8,067,182 | B2 | 11/2011 | Kelley et al. |
| 8,895,707 | B2 | 11/2014 | Cummings |
| 8,951,807 | B2 | 2/2015 | Cummings et al. |
| 9,212,203 | B2 | 12/2015 | Cummings et al. |
| 9,802,822 | B2 | 10/2017 | Cummings |
| 9,815,695 | B2 | 11/2017 | Cummings et al. |
| 9,914,749 | B2 | 3/2018 | Cummings et al. |
| 2004/0254267 | A1 | 12/2004 | Nagae |
| 2004/0265298 | A1 | 12/2004 | Lin |
| 2005/0107594 | A1 | 5/2005 | Sun et al. |
| 2005/0209100 | A1 | 9/2005 | Duval et al. |
| 2006/0246544 | A1 | 11/2006 | Kang et al. |
| 2007/0060741 | A1 | 3/2007 | Kelley et al. |
| 2009/0047723 | A1 | 2/2009 | Jensen et al. |
| 2009/0186396 | A1 | 7/2009 | Gagnon |
| 2009/0187005 | A1 | 7/2009 | Gagnon |
| 2009/0264651 | A1 | 10/2009 | Daly |
| 2009/0318674 | A1 | 12/2009 | Gagnon |
| 2010/0113751 | A1 | 5/2010 | Sun et al. |
| 2010/0291059 | A1 | 11/2010 | Sakuraba et al. |
| 2012/0149636 | A1 | 6/2012 | Kraynov et al. |
| 2012/0192901 | A1 | 8/2012 | Cummings |
| 2013/0323812 | A1 | 12/2013 | Cummings et al. |
| 2015/0367252 | A1 | 12/2015 | Snyder et al. |
| 2018/0022608 | A1 | 1/2018 | Cummings |
| 2018/0086638 | A1 | 3/2018 | Cummings et al. |
| 2018/0155390 | A1 | 6/2018 | Cummings et al. |

FOREIGN PATENT DOCUMENTS

| | | | |
|---|---|---|---|
| EP | 2138505 | B1 | 8/2014 |
| WO | 03/059935 | A2 | 7/2003 |
| WO | 06/099308 | A2 | 9/2006 |
| WO | 2008/025748 | A1 | 3/2008 |
| WO | 2008/113011 | A2 | 9/2008 |
| WO | 2009/017491 | A1 | 2/2009 |
| WO | 2010/034442 | A1 | 4/2010 |
| WO | 2010/148143 | A1 | 12/2010 |

OTHER PUBLICATIONS

U.S. Appl. No. 13/205,354, filed Aug. 8, 2011, Issued.
U.S. Appl. No. 13/891,502, filed May 10, 2013, Issued.
U.S. Appl. No. 14/598,719, filed Jan. 16, 2015, Issued.
U.S. Appl. No. 14/747,221, filed Jun. 23, 2015, Allowed.
U.S. Appl. No. 14/747,181, filed Jun. 23, 2015, Issued.
U.S. Appl. No. 14/932,080, filed Nov. 4, 2015, Issued.
U.S. Appl. No. 15/719,958, filed Sep. 29, 2017, Pending.
U.S. Appl. No. 15/725,473, filed Oct. 5, 2017, Pending.
U.S. Appl. No. 15/879,239, filed Jan. 14, 2018, Pending.
Bankston et al. "pH Transients in hydroxyapatite chromatography columns—Experimental evidence and phenomological modeling", Journal of Chromatography A, 1217 (2010) 2123-2131.
Britsch, "Purification of Flavanone 3 beta-Hydroxylase from Petunia hybrida: Antibody preparation and Characterization of a Chemogenetically Defined Mutant", Archives of Biochemistry and Biophysics, 276(2):348-354 (1990).
CHT Ceramic Hydroxyapatite: Instruction Manual, 16 pages (2001) http://www.bio-rad.com/cmc_upload/0/000/039/227/Lit-611d.pdf.
Gorbunoff et al.; "The interaction of proteins with hydroxyapatite—I. Role of protein charge and structure"; 1984, Analytical Biochemistry, vol. 136, No. 2, pp. 425-432.
Larsen et al., "Solubility Study of the Initial Formation of Calcium Orthophosphates from Aqueous Solutions at pH5-10", Arch Oral Biol., vol. 31, No. 9, pp. 565-572 (1986).
Recillas et al., "Studies on the precipitation behavior of calcium phosphate solutions", Journal of Ceramic Processing Research, vol. 13, No. 1, pp. 5-10 (2012).
Schroder et al., "Hydroxyapatite chromatography: altering the phosphate-dependent elution profile of protein as a function of pH", Analytical Biochemistry, vol. 313, pp. 176-178 (2003).
The International Search Report from PCT/US2011/021158, dated Mar. 17, 2011.
The International Search Report from PCT/US2011/048082, dated Mar. 20, 2012.
U.S. Appl. No. 13/006,022, filed Jan. 13, 2011 (25 pages).
U.S. Appl. No. 13/205,354, filed Aug. 8, 2011 (26 pages).
U.S. Appl. No. 13/891,502, filed May 10, 2013 (30 pages).
Extended European Search Report dated Dec. 17, 2014 for EP Application No. 11818724.4, 7 pages.
Extended European Search Report dated Dec. 17, 2015 for EP Application No. 13796784.0.
Extended European Search Report dated Jul. 21, 2014 for EP Application No. 11733384.9, 7 pages.
International Search Report and Written Opinion from PCT/US2013/40591, dated Oct. 8, 2013, 12 pages.
International Search Report and Written Opinion from PCT/US2015/037112, dated Sep. 29, 2015.
International Search Report and Written Opinion from PCT/US2015/037116, dated Sep. 16, 2015, 12 pages.
International Search Report and Written Opinion from PCT/US2015/0371456, dated Oct. 6, 2015.
U.S. Appl. No. 14/598,719, filed Jan. 16, 2015 (32 pages).
U.S. Appl. No. 14/932,080, filed Nov. 4, 2015 (22 pages).
U.S. Appl. No. 14/747,181, filed Jun. 23, 2015 (40 pages).
U.S. Appl. No. 14/747,221, filed Jun. 23, 2015 (35 pages).
CFT Ceramic Fluoroapatite. Instruction Manual. Bio-Rad Laboratories, Inc. Jan. 9, 2012 (date obtained from WayBackMachine).

US 10,583,371 B2

APATITE IN-SITU RESTORATION

CROSS-REFERENCES TO RELATED APPLICATIONS

This application is a continuation application of U.S. patent application Ser. No. 14/747,162, filed Jun. 23, 2015, which claims priority to U.S. Provisional Application No. 62/015,894, filed Jun. 23, 2014; and U.S. Provisional Application No. 62/082,017, filed on Nov. 19, 2014, each of which is incorporated in its entirety herein for all purposes.

BACKGROUND OF THE INVENTION

Apatite solid support surfaces, including hydroxyapatite, ceramic apatite, fluorapatite, and fluoride enhanced apatite, among other apatite solid surfaces, are used for purification of a wide variety of target analytes. Apatite is most commonly utilized for purification of biological analytes, including proteins, carbohydrates, polynucleotides, and viral particles. Apatite possesses unique properties as a purification support because it provides affinity, cation, and anion exchange modalities in a single support. Apatite purification can generally be performed in two ways: (i) flow through purification; and (ii) bind and elute purification.

For flow through purification, traditionally, one (a) equilibrates the column in a suitable buffer; (b) adds a sample to a column under conditions in which impurities bind to the column and the target molecule flows through and is collected, (c) cleans, or strips, the column to remove adsorbed biological compounds with a cleaning/stripping solution (e.g., a high molarity phosphate solution), and (d) regenerates, or sanitizes, the column with a strong alkaline hydroxide solution so that the column can be re-used. In some cases, the strong alkaline hydroxide solution is replaced with a low molarity rinse for long term storage or re-equilibration.

For bind and elute purification, traditionally, one (a) equilibrates the column in a suitable buffer; (b) adds a sample to a column under conditions in which the target molecule binds to the column, (c) elutes the target molecule (e.g., with a high molarity phosphate and/or alkaline halide solution), (d) cleans, or strips, the column to remove adsorbed biological compounds with a cleaning solution (e.g., a high molarity phosphate solution), and (e) regenerates, or sanitizes, the column with a strong alkaline hydroxide solution so that the column can be re-used. In some cases, the strong alkaline hydroxide solution is replaced with a low molarity rinse for long term storage or re-equilibration.

These traditional apatite purification methods can suffer from poor reproducibility and/or premature apatite deterioration. In some cases, this deterioration is due to the accumulation of hydronium ions (H3O+) on the apatite surface during exposure to equilibration, loading, or chromatography buffers. Hydronium ion accumulation can occur during exposure to alkali metal salts at a pH of 8.0 or below. Hydronium ion accumulation can also occur during exposure to phosphate buffers at a pH of less than about 6.5. Other buffer compositions can also cause hydronium ion accumulation. These hydronium ions are then desorbed upon exposure to a subsequent buffer, such as an elution buffer (e.g., during bind and elute purification) or a cleaning/stripping buffer (e.g., after flow through purification). This desorption causes the resin to deteriorate over time, resulting in a loss of resin mass and/or a decline in the particle strength of the resin.

BRIEF SUMMARY OF THE INVENTION

The present inventor has discovered that the deterioration of an apatite solid surface during, or subsequent to, a chromatographic procedure for purifying a target molecule from a sample can be surprisingly reduced, eliminated, or reversed by treating the apatite solid surface with a buffered calcium solution, followed by a phosphate buffered solution, followed by an alkaline hydroxide. The buffered calcium solution, phosphate buffered solution, and alkaline hydroxide can be applied subsequent to a bind and elute or flow through purification procedure.

In one aspect, the present invention provides a method of purifying a target analyte with an apatite solid surface, the method comprising: (a) contacting the apatite solid surface with the target analyte, thereby separating the target analyte from one or more contaminants; (b) collecting the target analyte; and (c) regenerating the apatite solid surface the regenerating comprising, (i) contacting the apatite solid surface with a buffered calcium solution comprising a calcium ion at a concentration of at least about 5 mM and a buffer, wherein the ratio of buffer concentration to calcium ion concentration is at least about 1, 1.5, or 2, and the pH of the solution is at least about 5, 5.1, 5.2, 5.3, 5.4, or 5.5; (ii) contacting the apatite solid surface with a phosphate buffered solution at a pH of at least about 6.5; and (iii) contacting the apatite solid surface with a solution comprising an hydroxide. In one embodiment, the buffer is a zwitterionic buffer. In one embodiment, the buffer is a phosphate buffer.

In one embodiment, the present invention provides a method of purifying a target analyte with an apatite solid surface, the method comprising: (a) contacting the apatite solid surface with the target analyte, thereby separating the target analyte from one or more contaminants; (b) collecting the target analyte; and (c) regenerating the apatite solid surface the regenerating comprising, (i) contacting the apatite solid surface with a buffered calcium solution comprising a calcium ion at a concentration of at least about 10 mM and a zwitterionic buffer, wherein the ratio of zwitterionic buffer concentration to calcium ion concentration is at least about 2, and the pH of the solution is at least about 6.5; (ii) contacting the apatite solid surface with a phosphate buffered solution at a pH of at least about 6.5; and (iii) contacting the apatite solid surface with a solution comprising an hydroxide.

In one embodiment, the present invention provides a method wherein (a) comprises binding the target analyte to the apatite solid surface, and (b) comprises eluting the target analyte from the apatite solid surface. In another embodiment, (a) comprises contacting the apatite solid surface to the target analyte, thereby flowing the target analyte through the apatite solid surface, and (b) comprises collecting the target analyte in the flow through.

In some cases, the zwitterionic buffer is a sulfonic acid containing buffer. In some cases, the sulfonic acid containing buffer is MES, PIPES, ACES, MOPSO, MOPS, BES, TES, HEPES, DIPSO, TAPS, TAPSO, POPSO, or HEPPSO, EPPS, CAPS, CAPSO, or CHES. In some cases, the sulfonic acid containing buffer is MES.

In one embodiment, the calcium ion is at least about 1 mM, 2 mM, 3 mM, 4 mM, 5 mM, 10 mM (e.g., 10.1 mM, 10.2 mM, 10.3 mM, 10.4 mM, or 10.5 mM), 20 mM, 25 mM or at least about 50 mM. In another embodiment, the ratio of buffer concentration (e.g., zwitterionic buffer concentration) to calcium ion concentration is at least about 2.5, 3, or 4. In yet another embodiment, the buffered calcium solution comprises calcium chloride or calcium nitrate. In yet another embodiment, the phosphate buffered solution comprises a solution containing from about 0.1 M or 0.2 M to about 1.0 M phosphate, or from about 0.1 M or 0.2 M to about 0.5 M phosphate, at a pH of from about 6.5 to about 8. In some cases, the phosphate buffered solution comprises 400 mM phosphate at a pH of 7.0.

In one embodiment, the hydroxide comprises an alkaline hydroxide. In some cases, the alkaline hydroxide comprises sodium or potassium hydroxide. In one embodiment, the regenerating reverses or eliminates degradation of the column that occurs during protein purification or column cleaning steps. In another embodiment, the regenerating increases the strength of the apatite solid surface by at least about 1%, 5%, 10%, 15%, 20%, or more.

In one embodiment the regenerating is performed before, or replaces, a phosphate cleaning/stripping step that elutes adsorbed biological compounds. In some cases, the regenerating step is performed after elution of target analyte.

In one embodiment, the (ii) contacting the apatite solid surface with a solution comprising phosphate at a pH of at least about 6.5 further comprises: contacting the apatite solid surface with a solution comprising phosphate at a concentration of 10 mM, or less than about 10 mM, at a pH of at least about 6.5 or 7; and then contacting the apatite solid surface with a solution comprising phosphate at a concentration of at least about 100 mM, 200 mM, 400 mM, or 500 mM, at a pH of at least about 6.5 or 7.

In one embodiment, the regenerating consists of (i), a wash, (ii), and (iii).

DEFINITIONS

Figure 1:
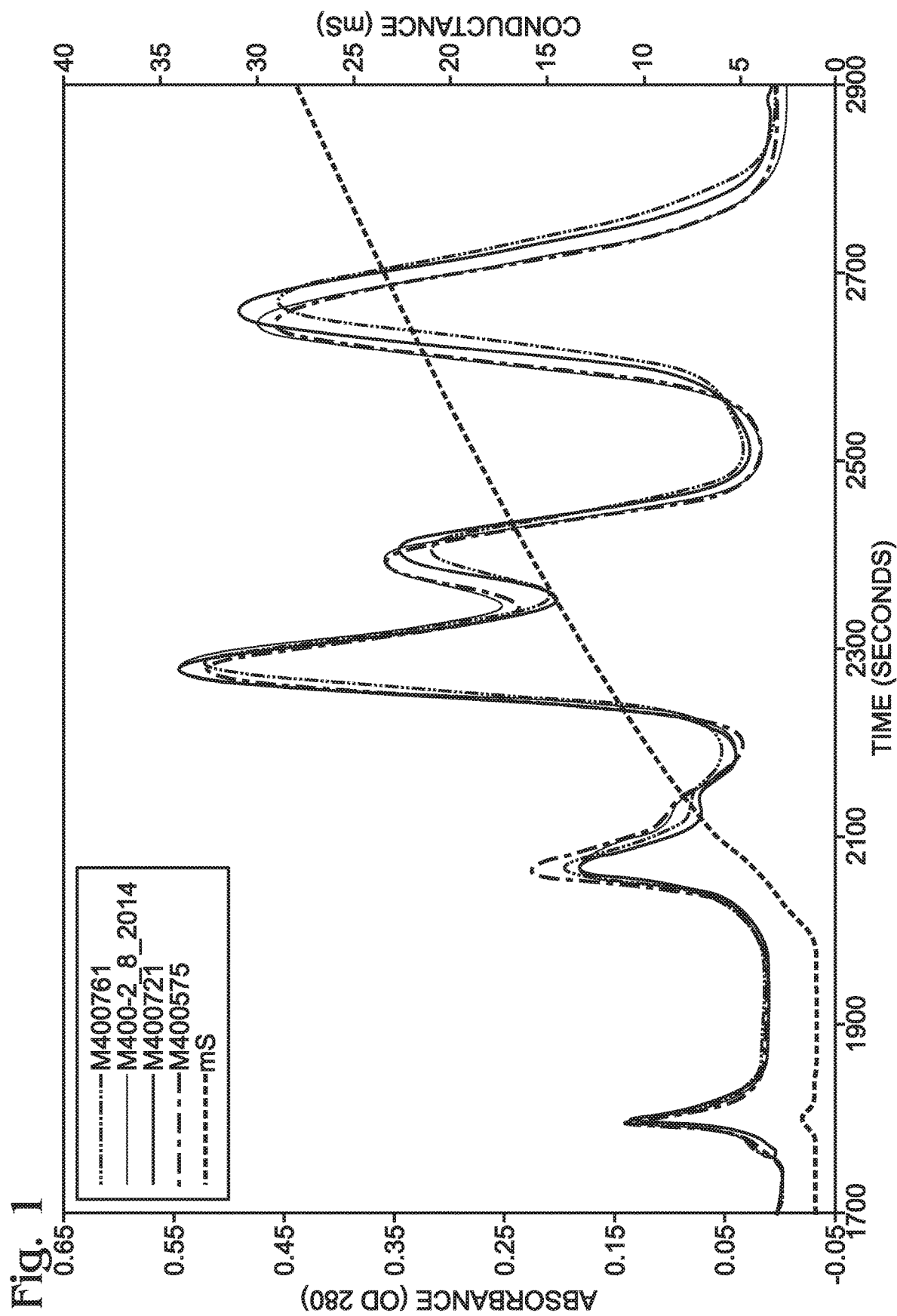
FIG. 1: depicts results from performing the apatite purification profile of Example 7, Table X.

"Apatite" refers to a mineral of phosphate and calcium of the general formula $Ca_5(PO_4)_3(X)$, wherein X is a negatively charged ion. Generally, X is F, Cl, or OH. However, the structure and chemistry of apatite allow for numerous substitutions, including a variety of metal cations (e.g., one or more of K, Na, Mn, Ni, Cu, Co, Zn, Sr, Ba, Pb, Cd, Sb, Y, U, or various rare earth elements) that substitute for Ca in the structure, and anionic complexes (e.g., $AsO_4^{-3}$, $SO_4^{-2}$, $CO_3^{-2}$, $SiO_4^{-4}$, etc.) that substitute for $PO_4^{-3}$.

"Hydroxyapatite" refers to a mixed mode solid support comprising an insoluble hydroxylated mineral of calcium phosphate with the structural formula $Ca_{10}(PO_4)_6(OH)_2$. Its dominant modes of interaction are phosphoryl cation exchange and calcium metal affinity. Hydroxapatite is commercially available in various forms, including but not limited to ceramic, crystalline and composite forms. Composite forms contain hydroxyapatite microcrystals entrapped within the pores of agarose or other beads.

"Fluorapatite" refers to a mixed mode support comprising an insoluble fluoridated mineral of calcium phosphate with the structural formula $Ca_{10}(PO_4)_6F_2$. Its dominant modes of interaction are phosphoryl cation exchange and calcium metal affinity. Fluorapatite is commercially available in various forms, including but not limited to ceramic and crystalline composite forms.

An "apatite solid surface" refers to fused nanocrystals (ceramic apatite), microcrystals, or compounded microcrystals of apatite. Apatite solid surfaces include, but are not limited to, hydroxyapatite, or fluorapatite. Ceramic apatites include, but are not limited to, ceramic hydroxyapatite (e.g., CHT™) or ceramic fluorapatite. Ceramic apatites are a form of apatite minerals in which nanocrystals are agglomerated into particles and fused at high temperature to create stable ceramic microspheres suitable for chromatography applications. Compounded microcrystals include but are not limited to HA Ultragel® (Pall Corp.). Microcrystals include but are not limited to Bio-Gel HTP, Bio-Gel® HT, DNA-Grade HT (Bio-Rad) and Hypatite C (Clarkson Chromatography).

"Sample" refers to any composition having a target molecule or particle of interest. A sample can be unpurified or partially purified. Samples can include samples of biological origin, including but not limited to blood, or blood parts (including but not limited to serum), urine, saliva, feces, as well as tissues. Samples can be derived from unpurified, partially purified, or purified cell lysate or spent cell growth media.

Deterioration of a resin that occurs upon use can cause the resin particles to lose their strength and thus to break apart into smaller particles causing blockage in the column. The deterioration can occur as a chemical breakdown of the apatite, causing a loss of mass which can in turn result in a loss of column volume, a loss in particle strength, an increase in particle breakage, or a combination thereof. In some embodiments of the present invention, such effects can be reversed by the present invention. The reversal of deterioration that can be achieved by the practice of the present invention can result in a lower rate of resin mass loss, a lower rate of decline in particle strength, or both. In many cases, the reversal of deterioration can be accompanied by increases in resin mass, particle strength, or both.

Mass of the apatite solid surface can be assayed by, e.g., weighing a dried apatite sample, for example after washing away buffer components and adsorbed biological compounds. Apatite media strength can be assayed by, e.g., measuring resistance to agitational force (e.g., stirring), resistance to sonication, or resistance to compression (e.g., application of a uniaxial compressive force). Resistance to sonication or agitational force can be measured by inspection of the apatite solid surface after the treatment to measure the generation of fines. Resistance to compression can be measured by measuring the force required to compress a given mass of apatite to a constant terminal force setting and determining the compressed distance. Apatite deterioration or degradation can be measured relative to a sample that has not been subjected to an apatite purification (i.e., purification of a target molecule using apatite) or an apatite regeneration procedure.

An "alkaline hydroxide" refers to a metal alkali hydroxide comprising any cation elements in Group I of the periodic table, including, e.g., lithium (Li), sodium (Na), potassium (K), rubidium (Rb), cesium (Cs), and francium (Fr). Thus, exemplary alkaline hydroxides include, for example, NaOH, LiOH, and KOH.

A zwitterionic buffer is a buffer that can contain a formal positive and a formal negative electrical charge at the same time. Exemplary zwitterionic buffers can include, but are not limited to, buffers containing a sulfonic acid group. As used herein, a "sulfonic acid" refers to a member of the class of organosulfur compounds with the general formula $RS(=O)_2$—OH, where R is an organic group (e.g., alkyl, or alkene, or aryl) and the $S(=O)_2$—OH group is a sulfonyl hydroxide.

Exemplary zwitterionic buffers containing a sulfonic acid group can include, but are not limited to, aminoalkanesulfonic acids. Exemplary aminoalkanesulfonic acids can include, but are not limited to, aminoalkanesulfonic acids with a minimum of two carbons between amine and sulfonic acid groups. Exemplary zwitterionic buffers containing a sulfonic acid group can include, but are not limited to, N,N-dialkylaminomethanesulfonic acids.

Exemplary zwitterionic buffers containing a sulfonic acid group can include, but are not limited to, MES (2-(N-morpholino)ethanesulfonic acid), PIPES (1,4-Piperazinediethanesulfonic acid), ACES (2-(carbamoylmethylamino)ethanesulfonic acid), MOPSO (3-morpholino-2-hydroxypropanesulfonic acid), MOPS (3-morpholinopropane-1-sulfonic acid), BES (N,N-Bis(2-hydroxyethyl)-2-aminoethanesulfonic acid), TES (2-[[1,3-dihydroxy-2-(hydroxymethyl)propan-2-yl]amino]ethanesulfonic acid), HEPES (2-[4-(2-hydroxyethyl)piperazin-1-yl]ethanesulfonic acid), DIPSO (3-(N,N-Bis[2-hydroxyethyl]amino)-2-hydroxypropanesulfonic acid), TAPS (3-[[1,3-dihydroxy-2-(hydroxymethyl)propan-2-yl]amino]propane-1-sulfonic acid), TAPSO (3-[[1,3-dihydroxy-2-(hydroxymethyl)propan-2-yl]amino]-2-hydroxypropane-1-sulfonic acid), POPSO (piperazine-1,4-bis(2-hydroxypropanesulfonic acid)), or HEPPSO (N-(2-Hydroxyethyl)piperazine-N'-(2-hydroxypropanesulfonic acid)), EPPS (N-(2-Hydroxyethyl)piperazine-N'-(3-propanesulfonic acid)), CAPS (3-(Cyclohexylamino)-1-propanesulfonic acid), CAPSO (N-cyclohexyl-2-hydroxyl-3-aminopropanesulfonic acid), CHES (2-(Cyclohexylamino)ethanesulfonic acid), MOBS (4-(N-morpholino)butanesulfonic acid), TABS (N-tris(hydroxymethyl)-4-aminobutanesulfonic acid), or AMPSO (N-(1,1-Dimethyl-2-hydroxyethyl)-3-amino-2-hydroxypropanesulfonic acid).

Calcium ion for use as a restoration material in the procedures described herein can be supplied by calcium hydroxide or by a soluble calcium salt, typically a salt that is soluble in water. Calcium halides and calcium nitrate are examples of calcium salts that can be used. An exemplary calcium halide is calcium chloride. In some cases, calcium chloride is preferred when the chromatography buffer during flow through purification, or the elution buffer during bind and elute purification, contains an alkali metal chloride.

As used herein, the terms "buffer," "buffered," and the like, in the context of a buffered calcium solution refers to a buffer that is compatible with (e.g., does not substantially interact with or precipitate in complex with) calcium under the specified conditions and is employed for the purpose of stabilizing the pH of an aqueous solution at or near a specified value, or within a specified range. As such, generally, the "buffer" in a buffered calcium solution cannot be water. In some embodiments, the "buffer" in a buffered calcium solution is not phosphate. In some embodiments, the "buffer" in a buffered calcium solution is phosphate. In some embodiments, the "buffer" in a buffered calcium solution used in an in situ regeneration protocol (e.g., after (e.g., immediately after) elution or target analyte flow through, or after (e.g., immediately after) elution or target analyte flow through and a wash) does not contain an alkali metal salt (e.g., sodium chloride), or contains less than about 0.1, 0.05, or 0.01 M alkali metal salt.

Phosphate can be used in a variety of buffers for apatite equilibration, chromatography, elution, cleaning/stripping, or apatite regeneration. Phosphate can be supplied from any soluble phosphate salt, typically a salt that is soluble in water. Alkali metal or alkaline earth metal phosphates are examples, with sodium or potassium phosphate as particularly convenient examples. Alkali or alkaline earth metal phosphate salts can be utilized in mono- and di-basic forms, or a combination thereof.

As used herein, the term "about" refers to the recited number and any value within 10% of the recited number. Thus, "about 5" refers to any value between 4.5 and 5.5, including 4.5 and 5.5.

DETAILED DESCRIPTION OF THE INVENTION

I. Introduction

Traditional apatite protein purification procedures generally either do not protect the apatite solid surface from deterioration, or seek to prevent deterioration. Methods that seek to prevent deterioration include the use of one or more common ions (e.g., U.S. application Ser. No. 13/205,354), or the use of a high pH phosphate solution (e.g., U.S. application Ser. No. 10/327,495). The presence of an ionic species in the buffer that is common to a component of the apatite solid surface (a common ion) can suppress leaching of that component from the apatite solid surface. Thus, calcium and/or phosphate buffers are often preferred during apatite equilibration, loading, flow through, elution, or cleaning/stripping. A high pH phosphate solution can function as a common ion, as well as minimizing potentially damaging pH excursions.

Other methods that seek to prevent deterioration include neutralization of accumulated hydronium ions prior to their release from the apatite solid surface during the apatite purification procedure. Neutralization can be performed with a strong base, such as an alkaline hydroxide (e.g., U.S. application Ser. No. 13/363,670). Neutralization can also be performed with a basic amino compound or sulphonated amine compound (e.g., U.S. application Ser. No. 13/006,022). Accumulation of hydronium ions on the apatite surface can occur due to a variety of mechanisms during equilibration, loading, flow through, and washing steps.

In particular, the presence of alkali metal salts can increase, or promote, accumulation of hydronium ions. A high pH phosphate solution (e.g., phosphate at a pH of about 6.5 or higher) of sufficient concentration (e.g., 100, 200, 300, 400 mM, or higher), can provide buffering capacity to mitigate the pH shift that commonly occurs during hydronium ion release, and therefore reduce acid solubilization of the apatite. The use of alkali metal salts concurrently with a phosphate buffer of at a suitable pH and concentration generally mitigates mass loss to a significant degree. However, media strength can still be significantly decreased. Neutralization of accumulated hydronium ions can reduce the amount of accumulated hydronium ions, and thus reduce degradation during a subsequent phosphate buffer cleaning step.

The present invention is based on the surprising discovery that an apatite solid surface can be significantly regenerated by treating with a buffered calcium regeneration solution. Generally, the buffered calcium solution is applied after the target molecule has been purified and collected. In some cases, the buffered calcium solution is applied after the apatite solid surface has been cleaned/stripped (e.g., with a high molarity phosphate buffer, such as 100, 200, 300, 400, or 500 mM phosphate, or higher) and/or sanitized (e.g., with alkaline hydroxide at a concentration of about 0.1, 0.5, or 1 M). The buffered calcium solution can be optionally washed away. In some cases, the apatite is then treated with a phosphate buffered solution (e.g., a phosphate buffered solution that does not contain calcium). In some cases, the phosphate buffered solution applied after the buffered calcium solution contains a higher concentration of phosphate than in the buffered calcium solution. In some cases, the order of the buffered calcium regeneration solution and the phosphate buffered regeneration solution is reversed.

After contacting the phosphate buffered solution with the apatite solid surface, the apatite solid surface can be further treated with an hydroxide. The regeneration procedures described herein (e.g., contacting apatite with a buffered calcium solution, then phosphate buffered solution, and then alkaline hydroxide; or contacting apatite with a phosphate buffered solution, then a buffered calcium solution, and then alkaline hydroxide) provide a substantial and surprising degree of regeneration. This substantial and surprising degree of regeneration can be indicated as a reduction, elimination, or reversal of degradation, as measured by change (e.g., loss) in apatite mass or loss in apatite strength. In some cases, regeneration can be indicated as a maintenance, or decrease in loss of chromatographic resolution or selectivity. In some cases, the regeneration methods described herein can be combined with one or more methods that reduce or prevent degradation, such as those described in the paragraphs above.

Selectivity can be measured as a ratio of retention volumes (e.g., adjusted for dead volume) between two different components in a mixture. Resolution can be measured as the ratio of the distance between two chromatographic peak maxima to the mean value of the peak width at base line between two different components in a mixture. In some cases, the components are protein chromatography standards. Exemplary protein chromatography standards include, but are not limited to, ovalbumin, myoglobin, alpha chymotrypsinogen a, or cytochrome c.

II. Methods

Described herein, are apatite regeneration methods for reducing, eliminating, or reversing apatite deterioration by treating the apatite solid surface with a buffered calcium solution, followed by a phosphate buffered solution, followed by an alkaline hydroxide. The buffered calcium solution, phosphate buffered solution, and alkaline hydroxide can be applied subsequent to a bind and elute or flow through purification procedure.

In some embodiments, a sample is contacted with an apatite solid surface (e.g., an equilibrated apatite solid surface), the target molecule is collected (e.g., during flow through purification, or after elution), and the apatite is regenerated by contacting the apatite solid surface with a buffered calcium solution, followed by a phosphate buffered solution, followed by an alkaline hydroxide. In some cases, the apatite solid surface is used multiple times for target analyte purification prior to application of one or more regeneration steps described herein.

In some embodiments, the apatite solid surface is washed or rinsed prior to regenerating. In other embodiments, the apatite solid surface is not washed or rinsed prior to regenerating. In some cases, the resin is treated with a wash solution to remove any excess calcium, phosphate, or hydroxide ions. One of skill in the art can readily select a suitable wash buffer. Generally, the wash buffer can be at a pH, composition, and concentration that does not substantially leach components of the apatite surface, release accumulated hydronium ions, or generate undesirable precipitate. For example, the wash buffer can be compatible, and thus not precipitate when mixed, with the preceding and subsequent buffer. Suitable washing buffers can include buffer compositions typically used for equilibration, loading, or flow through of apatite. In some cases, the apatite solid surface is washed with a low molarity phosphate buffer (e.g., phosphate at a concentration of less than about 100 mM, 50 mM, 25 mM, 20 mM, 15 mM, 10 mM, or 5 mM). The pH of the wash buffer can be at least about 5, 5.1, 5.2, 5.3, or 5.4, at least about 5.5, at least about 6, or at least about 6.5, 7, or 8. An exemplary wash buffer pH is 5.5, 6, or 6.5. In some cases, a water wash is applied, and the amounts can vary widely. A typical water wash will be at least about 0.2 resin volumes, and in most cases from about 0.2 to about 1.5 or from about 0.2 to about 2 resin volumes.

The apatite solid surface can then be regenerated. In some cases, the apatite solid surface can be regenerated, e.g., after elution, after flow through, after neutralization, after cleaning/stripping, after rinsing, or after storage. In some cases, the apatite solid surface can be regenerated after a wash, e.g., after application of a wash buffer to remove a flow through, elution, neutralization, rinsing, storage, or cleaning/stripping buffer.

A. Buffered Calcium Solution

The regeneration begins with contacting the apatite solid surface with a buffered calcium solution. Although, regeneration of the apatite solid surface has been attempted using an unbuffered calcium solution, the present inventors have found that the use of a buffered calcium solution appears to significantly and surprisingly enhance the degree of regeneration obtained. The calcium ion concentration of the buffered calcium solution and the amount of the buffered calcium solution passed through the resin can vary, but will generally be selected as any amount that will reduce, eliminate, or reverse the deterioration of the resin that occurs during apatite use (e.g., during purification, during elution, or during cleaning/stripping).

Without wishing to be bound by theory, it is believed that the buffered calcium solution interacts with the apatite solid surface to generate a loosely bound (e.g., non-covalent) calcium layer on the apatite solid surface. In some cases, this calcium layer replaces some or all (or more than all) of the calcium lost during previous purification steps. Thus, an amount, volume, concentration, etc. of calcium ion, or any other component or aspect of the buffered calcium solution that will reduce, eliminate, or reverse the deterioration of the resin that occurs during apatite use, can be an amount that allows for sufficient formation of a loosely bound calcium layer.

The calcium ion concentration is generally selected to be below the solubility limit of calcium at the pH and temperature of the buffered calcium solution. Moreover, the concentration can vary based on the presence, absence, or concentration of other components in the buffered calcium solution, such as the selected buffering agent, or based on the selected composition of any preceding buffer. In certain embodiments of the concepts herein, best results will be achieved with a calcium ion concentration of from about 5 mM, 5.1 mM, 5.2 mM, 5.3 mM, 5.4 mM, 5.5 mM, 5.6 mM, 5.7 mM, 5.8 mM, 5.9 mM, 6 mM, 6.5 mM, 7, mM, 8 mM, 9 mM, 10 mM, 10.1 mM, 10.2 mM, 10.3 mM, 10.5 mM, or 11 mM to about 15 mM, 20 mM, 25 mM, 30 mM, 40 mM, 50 mM, 75 mM, 100 mM, or 250 mM. In certain embodiments, the calcium ion concentration in the buffered calcium solution is from about 5 mM to about 10 mM, from about 5 mM to about 25 mM, from about 20 mM to about 100 mM, or from about 25 mM to about 50-75 mM, including 5 mM, 5.1 mM, 5.2 mM, 5.3 mM, 5.4 mM, 5.5 mM, 5.6 mM, 5.7 mM, 5.8 mM, 5.9 mM, 6 mM, 6.5 mM, 7, mM, 8 mM, 9 mM, 10 mM, 10.1 mM, 10.2 mM, 10.3 mM, 10.5 mM, 11 mM, 12 mM, 13 mM, 14 mM, 15 mM, 20 mM, 25 mM, 30 mM, 40 mM, 60 ppm, 70 mM, 80 mM, 90 mM, 110 mM, 150 mM, 200 mM, 300 mM, or higher.

The volume of the solution needed to achieve the restoration can vary with the calcium ion concentration, but in most cases best results will be achieved with from about 1.0 to about 10.0 resin volumes of solution, and in many cases with about 1, 1.1, 1.2, 1.3, 1.4, 1.5, 1.6, 1.7, 1.8, 1.9, or about 2 resin volumes. In some cases, the volume can be up to about 6 resin volumes, including 2, 3, 4, or 5 resin volumes. In some cases, the volume is less than 3 column volumes. In some cases, a high calcium ion concentration at a volume that is less than a resin volume (e.g., less than about 0.9, 0.7, 0.5 volumes) can be utilized.

A wide variety of buffers are suitable for the buffered calcium solution for apatite regeneration. In some embodiments, a buffer for the buffered calcium solution that does not appreciably form metal complexes in solution (e.g., does not form a complex with calcium at the pH of the buffer solution) can comprise the buffer component of the buffered calcium solution. In some embodiments, a buffer that does not contain primary or secondary (i.e., $R_2$—N, wherein R is not H) amine can comprise the buffer component of the buffered calcium solution. In some embodiments, a zwitterionic buffer is preferred. In some embodiments, a buffer (e.g., a zwitterionic buffer) that contains a sulfonic acid moiety is preferred. In some embodiments, a buffer (e.g., a zwitterionic buffer) that contains a sulfonic acid and a tertiary amine (i.e., $R_3$—N, wherein R is not H) is preferred. Exemplary zwitterionic buffers suitable for use as a buffering agent in the buffered calcium solution include, but are not limited to, one or more of the following: MES, PIPES, ACES, MOPSO, MOPS, BES, TES, HEPES, DIPSO, TAPS, TAPSO, POPSO, or HEPPSO, EPPS, CAPS, CAPSO, CHES, MOBS, TABS, or AMPSO. In some embodiments, the buffer of the buffered calcium solution contains a primary, secondary, or a tertiary amine. In some embodiments, the buffer of the buffered calcium solution contains a primary, secondary or a tertiary amine and a one or more carboxylate or hydroxymethyl groups. In some embodiments, the buffer of the buffered calcium solution is tricine, bicine, or tromethamine. In some embodiments, the buffer of the buffered calcium solution is bis(2-hydroxyethyl)-amino-tris(hydroxymethyl)-methane), or 1,3-bis(tris (hydroxymethyl) methylamino) propane.

The buffer concentration in the buffered calcium solution can vary, but will generally be selected as a concentration that is at least as high as the calcium ion concentration of the solution. Moreover, the concentration can vary based on the selected buffering agent, or the selected composition of any preceding buffer. Thus, the ratio of the buffer concentration to the calcium ion concentration is generally at least about 1, e.g., 1, 1.1, 1.2, 1.3, 1.4, 1.5, 1.6, 1.7, 1.8, 1.9, 2, 2.1, 2.2, 2.5, 3, 4, 5, 6, 7, 8, 9, 10, or higher. Generally, the buffer concentration is also selected such that it is below the solubility limit of the buffering agent. In some cases, preferred buffering agents include those that have a high solubility limit.

The pH of the buffered calcium solution can vary, but will generally be selected as any amount that will reduce, eliminate, or reverse deterioration of the resin that occurs during apatite use (e.g., during purification, during elution, or during cleaning/stripping). Moreover, the pH can vary based on the selected apatite solid surface, the selected buffering agent, the selected concentration of one or more components, or the selected composition of any preceding buffer. Typically, the pH is, or is at least about, 5, 5.1, 5.2, 5.3, 5.4, 5.5, 5.6, 6, 6.2, 6.5, 7, 7.5, or 8. In some embodiments, the pH is, or is at least about, 5.5, 6, 6.5, 7, 7.5, or 8. In some embodiments, the pH is 5.5, 6, 6.5, 7, 7.5, or 8. In some embodiments, the pH is 5.1, 5.2, 5.3, or 5.4. In some cases, the pH is 5.3. In some cases, the pH is 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, or 7.5. In some cases, the pH is 7.0. In some cases, the pH is 5.6. In some cases, the pH is 6.2. In some cases, the pH is 5.4.

In some embodiments, the buffer of the buffered calcium solution is a phosphate buffer. In such cases, the calcium and phosphate concentrations and the pH of the solution can be selected to provide regeneration while avoiding precipitant formation, or avoiding a supersaturated solution. For example, the pH of the phosphate buffered calcium solution can be selected to be sufficiently low (e.g., a pH of about, or less than about, 6.5, 6.4, 6.3, 6.2, 6.1, 6, 5.9, 5.8, 5.7, 5.6, 5.5, 5.4, 5.3, 5.2, 5.1, or 5). In some cases, the pH is 5.1, 5.2, 5.3, 5.4, or 5.5. In some cases, the pH is 5.3. As another example, the calcium concentration of the phosphate buffered calcium solution can be about, or less than about, 50 mM, 40 mM, 35 mM, 30 mM, 25 mM, 20 mM, 15 mM, 10 mM, 7 mM, 6 mM, 5.9 mM, 5.8 mM, 5.7 mM, 5.6 mM, 5.5 mM, 5.4 mM, 5.3 mM, 5.2 mM, 5.1 mM, or 5 mM. In some cases, the calcium concentration of the phosphate buffered solution is, or is about, 15 mM, 14 mM, 13 mM, 12 mM, 11 mM, 10.5 mM, 10.4 mM, 10.3 mM, 10.2 mM, 10.1 mM, 10 mM, or 9.5 mM. In some cases, the calcium concentration is 10 or 10.2 mM. In some cases, the calcium concentration is 10 mM. As another example, the phosphate concentration of the phosphate buffered calcium solution can be about, or less than about, 50 mM, 40 mM, 35 mM, 30 mM, 29 mM, 28 mM, 27 mM, 26 mM, 25 mM, 24 mM, 23 mM, 21 mM, 20 mM, 18 mM, 17 mM, 16 mM, or 15 mM. In some cases, the use of a phosphate buffered calcium solution provides regeneration with or without a preceeding or subsequent high molarity (e.g., 0.1, 0.2, 0.3, 0.4, 0.5, 0.6, 0.7, 0.8, 0.9, or 1 M) phosphate buffer step.

In some embodiments, the apatite solid surface is in a column, e.g., a chromatography column, and the buffered calcium solution can be applied to the apatite solid surface at a flow rate. The flow rate can vary, but will generally be selected as any rate that will reduce, eliminate, or reverse deterioration of the resin that occurs during apatite use (e.g., during purification, during elution, or during cleaning/stripping). Suitable flow rates, include rates that are typically used during equilibration, loading, elution, cleaning/stripping, sanitation, or rinsing of apatite. An exemplary flow rate is 400 cm/hr. In some cases, the flow rate is substantially lower than 400 cm/hr (e.g., 300, 200, 100, or 50 cm/hr, or less). The use of a low flow rate can allow a greater contact time between the apatite solid surface and the buffered calcium solution. A low flow rate can be particularly preferred when the concentration of calcium or buffering agent, or the volume of the buffered calcium solution, is low. A low flow rate can also be preferred when the buffered calcium solution, or the preceding solution, is viscous or the column is fouled with adsorbed biological compounds. Alternatively, the flow rate can be higher than 400 cm/hr. In some cases, the formation of a loosely bound layer of calcium is rapid and a high flow rate can advantageously reduce the time required for apatite regeneration.

In some embodiments, the apatite solid surface is contacted with the buffered calcium solution in a batch format. In a batch format, the buffered calcium solution can be applied by pouring the buffered calcium solution onto the apatite solid surface, or pouring a slurry of the apatite solid surface into the buffered calcium solution. The contact time can vary, but will generally be selected as any time that will reduce, eliminate, or reverse deterioration of the resin that occurs during apatite use (e.g., during purification, during elution, or during cleaning/stripping).

In some embodiments, the apatite solid surface is then washed or rinsed. One of skill in the art can readily select a suitable wash buffer. In some cases, the resin is treated with a wash solution between the individual regeneration treatments to remove any excess calcium, phosphate, or hydroxide ions. Generally, the wash buffer can be at a pH, composition, and concentration that does not substantially leach components of the apatite surface, release accumulated hydronium ions, or generate undesirable precipitate. For example, the wash buffer can be compatible, and thus not precipitate when mixed, with the preceding and subsequent buffer. As another example, the wash buffer can be selected that does not leach any loosely bound calcium layer formed during the contacting of the apatite solid surface with the buffered calcium solution. Suitable washing buffers can include buffer compositions typically used for equilibration, loading, or flow through of apatite. In some cases, the apatite solid surface is washed with a low molarity phosphate buffer (e.g., phosphate at a concentration of less than about 100 mM, 50 mM, 25 mM, 20 mM, 15 mM, 10 mM, or 5 mM). The pH of the wash buffer can be at least about 5, at least about 5.5, at least about 6, or at least about 6.5, 7, or 8. In some cases, a water wash is applied, and the amounts can vary widely. A typical water wash will be at least about 0.2 resin volumes, and in most cases from about 0.2 to about 1.5 or from about 0.2 to about 2 resin volumes.

B. Phosphate Buffered Solution

The apatite solid surface can then be contacted with a phosphate containing buffer after the apatite has been contacted with a buffered calcium solution. Alternatively, the phosphate containing buffer can be contacted with apatite before the apatite has been contacted with a buffered calcium solution. In some cases, an intervening wash step is applied between the buffered calcium solution and the phosphate containing buffer. The phosphate concentration of the phosphate containing buffer and the amount of the phosphate containing buffer passed through the resin can vary, but will generally be selected as any amount that will reduce, eliminate, or reverse the deterioration of the resin that occurs during apatite use (e.g., during purification, during elution, or during cleaning/stripping). Without wishing to be bound by theory, it is believed that the phosphate containing buffer interacts with the apatite solid surface, or a loosely bound calcium layer formed during contact with the buffered calcium solution, to generate a loosely bound (e.g., non-covalent) phosphate layer on the apatite solid surface. In some cases, this phosphate layer replaces some or all (or more than all) of the phosphate lost during previous purification steps. Thus, an amount, volume, concentration, etc. of phosphate, or any other component or aspect of the phosphate containing buffer that will reduce, eliminate, or reverse the deterioration of the resin that occurs during apatite use, can be an amount that allows for sufficient formation of a loosely bound phosphate layer.

The phosphate concentration of the phosphate containing buffer is generally selected to be below the solubility limit of the phosphate at the pH and temperature of the buffer. Moreover, the concentration can vary based on presence or absence of other components of the buffer, or the selected composition of any preceding buffer. In certain embodiments of the concepts herein, best results will be achieved with a phosphate concentration of from about 10 mM to about 1, 1.5, or 2 M; from about 20 mM to about 1.5 M; or from about 25 mM to about 1 M; from about 50 mM to about 1 M; including at least about, or about, 10 mM, 15 mM, 20 mM, 25 mM, 30 mM, 40 mM, 50 mM, 60 ppm, 70 mM, 80 mM, 90 mM, 100 mM, 110 mM, 150 mM, 200 mM, 300 mM, 500 mM, 750 mM, 1 M, or higher. In some cases, the phosphate concentration is 10 mM, 15 mM, 20 mM, 25 mM, 30 mM, 40 mM, 50 mM, 60 ppm, 70 mM, 80 mM, 90 mM, 100 mM, 110 mM, 150 mM, 200 mM, 300 mM, 500 mM, 750 mM, 1 M, or higher. In some cases, the phosphate concentration is from, or from about, 0.1 or 2 M to, or to about, 0.4 M, 0.5 M, or 1 M. In some cases, the column is contacted with a low concentration phosphate buffer (e.g., 2, 5, 10, 15, 20, or 25 mM) and then a high concentration phosphate buffer (e.g., 30; 50; 75; 100; 250; 500; 750; 1,000; 1,500; or 2,000 mM). In some cases, the use of a low concentration phosphate buffer followed by a high concentration phosphate buffer can avoid potential incompatibility (e.g., precipitation) between the buffered calcium solution and the high concentration phosphate buffer.

The pH of the phosphate containing buffer and the amount of the phosphate containing buffer passed through the resin can vary, but will generally be selected as any pH that will reduce, eliminate, or reverse the deterioration of the resin that occurs during apatite use (e.g., during purification, during elution, or during cleaning/stripping). Exemplary pH values suitable for apatite regeneration with a phosphate containing buffer include any pH that is at least about 5, at least about 5.5, at least about 6, at least about 6.5, at least about 7, at least about 7.5, at least about 8, or at least about 8.5, or higher. In some cases, the pH of the phosphate containing buffer is 5, 5.5, 6, 6.5, 7, 7.5, 8, 8.5, 9, 9.5, 10, or higher.

The volume of the solution needed to achieve the restoration can vary with the phosphate ion concentration, but in most cases best results will be achieved with from about 1.0 to about 10.0 resin volumes of solution, and in many cases with about 1, 1.1, 1.2, 1.3, 1.4, 1.5, 1.6, 1.7, 1.8, 1.9, or about 2 resin volumes. The volume can be up to about 6 resin volumes, including 2, 3, 4, or 5 resin volumes. In some cases, a high phosphate concentration at a volume that is less than a resin volume (e.g., less than about 0.9, 0.7, 0.5 volumes) can be utilized.

In some embodiments, the apatite solid surface is in a column, e.g., a chromatography column, and the phosphate containing buffer can be applied to the apatite solid surface at a flow rate. The flow rate can vary, but will generally be selected as any rate that will reduce, eliminate, or reverse deterioration of the resin that occurs during apatite use (e.g., during purification, during elution, or during cleaning/stripping). Suitable flow rates, include rates that are typically used during equilibration, loading, elution, cleaning/stripping, sanitation, or rinsing of apatite. An exemplary flow rate is 400 cm/hr. In some cases, the flow rate is substantially lower than 400 cm/hr (e.g., 300, 200, 100, or 50 cm/hr, or less). The use of a low flow rate can allow a greater contact time between the apatite solid surface and the phosphate containing buffer. A low flow rate can be particularly preferred when the concentration of phosphate, or the volume of the phosphate containing buffer, is low. A low flow rate can also be preferred when the phosphate containing buffer, or the preceding solution, is viscous or the column is fouled with adsorbed biological compounds. Alternatively, the flow rate can be higher than 400 cm/hr. In some cases, the formation of a loosely bound layer of phosphate is rapid and a high flow rate can advantageously reduce the time required for apatite regeneration.

In some embodiments, the apatite solid surface is contacted with the phosphate containing buffer in a batch format. In a batch format, the phosphate containing buffer can be applied by pouring the phosphate containing buffer onto the apatite solid surface, or pouring a slurry of the apatite solid surface into the phosphate containing buffer. The contact time can vary, but will generally be selected as any time that will reduce, eliminate, or reverse deterioration of the resin that occurs during apatite use (e.g., during purification, during elution, or during cleaning/stripping).

In some embodiments, the apatite solid surface is then washed or rinsed. In other embodiments, the apatite solid surface is not washed or rinsed after regeneration treatment with a phosphate containing buffer. One of skill in the art can readily select a suitable wash buffer. In some cases, the resin is treated with a wash solution to remove any excess calcium, phosphate, or hydroxide ions. Generally, the wash buffer is at a pH, composition, and concentration that does not substantially leach components of the apatite surface, release accumulated hydronium ions, or generate undesirable precipitate. For example, the wash buffer can be compatible, and thus not precipitate when mixed, with the preceding and subsequent buffer. As another example, the wash buffer can be selected that does not leach any loosely bound calcium layer formed during the contacting of the apatite solid surface with the buffered calcium solution. Suitable washing buffers can include buffer compositions typically used for equilibration, loading, or flow through of apatite. In some cases, the apatite solid surface is washed with a low molarity phosphate buffer (e.g., phosphate at a concentration of less than about 100 mM, 50 mM, 25 mM, 20 mM, 15 mM, 10 mM, or 5 mM). The pH of the wash buffer can be at least about 5, at least about 5.5, at least about 6, or at least about 6.5, 7, or 8. In some cases, a water wash is applied, and the amounts can vary widely. A typical water wash will be at least about 0.2 resin volumes, and in most cases from about 0.2 to about 1.5 or from about 0.2 to about 2 resin volumes.

A degree of resin regeneration can be achieved with either the buffered calcium solution treatment preceding the phosphate containing buffer treatment, or with the phosphate containing buffer treatment preceding the buffered calcium solution treatment. In some embodiments, a greater degree of regeneration can be achieved by applying the buffered calcium solution treatment first, followed by the phosphate containing buffer treatment. In some embodiments, a preferred degree of regeneration can be achieved by performing one or more steps of buffered calcium solution treatment subsequent to, or followed by, one or more steps of phosphate containing buffer treatment. In some cases, one or more of multiple steps of buffered calcium solution treatment or phosphate containing buffer treatment are preceded by or followed by a wash.

In some embodiments, the buffered calcium solution treatment and/or the phosphate containing buffer treatment is applied after elution or flow through of a target analyte. For example an apatite surface can be equilibrated, contacted with a target analyte, the target analyte can be eluted or collected in the flow through, and then the regeneration protocol can be applied. As described herein, exemplary regeneration protocols can include, but are not limited to, those in which a buffered calcium solution is contacted with the apatite solid surface and then a phosphate buffer is contacted with the apatite solid surface. Exemplary regeneration protocols can further include, but are not limited to, those in which a phosphate regeneration buffer is contacted with the apatite solid surface and then a buffered calcium regeneration solution is contacted with the apatite solid surface. An alkaline hydroxide treatment can be applied after the apatite is contacted with the buffered calcium and phosphate regeneration solutions.

C. Hydroxide

The hydroxide ion treatment is applied as the last treatment step of the apatite solid surface regeneration. Any soluble form of hydroxide ion can be used, preferably a water-soluble form is used. In some cases, alkali metal hydroxides, such as sodium or potassium hydroxide, are particularly convenient. As in the cases of the calcium ion and the phosphate ion, the concentration and quantity of hydroxide ion solution can vary. Without wishing to be bound by theory, it is believed that the hydroxide interacts with the apatite solid surface, or loosely bound (e.g., non-covalently bound) calcium, phosphate, or calcium and phosphate layer(s) formed during contact with the buffered calcium solution and/or phosphate containing buffer, to convert the loosely bound (e.g., non-covalently bound) minerals into apatite, thus providing a regenerated surface. In some cases, this regenerated surface replaces some or all (or more than all) of the calcium, phosphate, or calcium phosphate lost during previous purification steps. Thus, an amount, volume, concentration, etc. of hydroxide that will reduce, eliminate, or reverse the deterioration of the resin that occurs during apatite use, can be an amount that allows for sufficient conversion of loosely bound calcium, phosphate, or calcium phosphate to apatite. The hydroxide ion can also clean the resin of residual proteins and contaminants and can also serve as a sanitation or storage solution.

The hydroxide ion concentration can be from about 0.005 or 0.01 M to about 5 M; about 0.1 M to about 4.0 M, and in many cases from about 0.3 M to about 3.0 M, including 0.2 M, 0.5 M, 0.75 M, 1.0 M, 1.25 M, 1.5 M, 2.0 M, or 2.5 M. Suitable volumes of hydroxide ion containing treatment solution range from about 1.0 to about 20.0 resin volumes, and in many cases from about 1.5 to about 10.0 resin volumes, including 2, 3, 4, 5, 6, 7, 8, or 9 volumes. In some cases, a high hydroxide concentration at a volume that is less than a resin volume (e.g., less than about 0.9, 0.7, 0.5 volumes) can be utilized.

Following hydroxide treatment, the resin can be washed or equilibrated with a suitable buffer. In some cases, the resin is equilibrated, or washed and then equilibrated, with a loading buffer. For example, the resin can be equilibrated with 10 mM phosphate buffer, pH 6.5 to equilibrate the column for protein purification. In some cases, the resin is equilibrated, or washed and then equilibrated, with a storage buffer. For example, the resin can be equilibrated with 0.1 M NaOH, 10 mM phosphate buffer and then stored.

EXAMPLES

The following examples are provided by way of illustration only and not by way of limitation. Those of skill in the art will readily recognize a variety of non-critical parameters that could be changed or modified to yield essentially the same or similar results.

Example 1—Control Experiment

This example illustrates the deterioration of a hydroxyapatite resin over a series of cycles exposing the resin to conditions that simulate those encountered in protein separations (but without loading and eluting protein). The experiment was performed on a column measuring 20 cm in length and 2.2 cm in internal diameter, with an internal volume of 76 mL, and the packing was ceramic hydroxyapatite Type I in 40-micron particles weighing approximately 48 grams, the resulting mobile phase flow rate through the column being 250 cm/h. A series of 25 consecutive cycles were performed, each cycle consisting of the following eight steps:

TABLE I

Treatment Protocol for Simulated Cycles of Separation and Column Restoration

| | | | Amount | | |
|---|---|---|---|---|---|
| Step | Description | Mobile Phase | Column Volumes | Volume in mL | Time in minutes |
| 1 | Rinse | Water | 1 | 76 | 4.8 |
| 2 | Pre-Equilibration | 400 mM NaPi, pH 7.0 | 3 | 228.1 | 14.4 |
| 3 | Equilibration | 10 mM NaPi, pH 6.8 | 6 | 456.2 | 28.8 |
| 4 | Equilibration | 10 mM NaPi, 1.0M NaCl, pH 6.5 | 6 | 456.2 | 28.8 |
| 5 | Rinse | Water | 2 | 152.1 | 9.6 |
| 6 | Regeneration | 400 mM NaPi, pH 7.0 | 2 | 152.1 | 9.6 |
| 7 | Rinse | Water | 1 | 76 | 4.8 |
| 8 | Sanitization | 1M NaOH | 2 | 152.1 | 9.6 |

In this protocol, Step 2 is a conditioning step to lower the pH of the column following the alkali treatment of Step 8; and Steps 3 and 4 expose the column to the conditions that are generally present during column equilibration, sample loading, and elution. Measurements of particle mass and particle strength (by uniaxial confined bulk compression, "UCBC") were taken before the first cycle and after the last cycle in each of three segments of the column—the top 25%, the middle 50%, and the bottom 25% (the mobile phase entry being at the top of the column). The results are listed in Table II below.

TABLE II

Changes in Solid Phase Mass and Strength at Three Column Locations for Simulated Cycles of Separation and Column Restoration

| | Resin Mass | | | Particle Strength (UCBC @ 6.00 mm) | | |
|---|---|---|---|---|---|---|
| Packing Location | Start | After 25 Cycles | Percent Change | N | psi | Percent Change |
| Top 25% | 12.00 g | 11.11 g | −7.42% | 136.9 | 516 | −49% |
| Middle 50% | 23.90 g | 22.26 g | −6.86% | 156.6 | 590 | −41% |
| Bottom 25% | 12.00 g | 11.23 g | −6.42% | 132.05 | 498 | −50% |
| Total | 47.90 g | 44.60 g | −6.89% | | | |
| | | | | Control: 266.4 | 1003 | |

The data in Table II indicate that the resin experienced chemical modification as evidenced by a significant loss of mass and a significant decline in particle strength. The overall mass loss was 6.89% and was approximately uniform throughout the height of the column. The decline in particle strength was greatest at the top and bottom, but generally extended throughout the column as well.

Example 2

This example illustrates the result of incorporating an in situ regeneration protocol without buffering the calcium regeneration solution. The experiment was performed on a column measuring 40 cm in length and 1.6 cm in internal diameter, with an internal volume of 80.42 mL, and the packing was ceramic hydroxyapatite Type I in 40-micron particles weighing approximately 51 grams, the resulting mobile phase flow rate through the column being 200 cm/h. A series of 25 consecutive cycles were performed, each cycle consisting of the following eleven steps:

TABLE III

Treatment Protocol for Simulated Cycles of Separation and Column Restoration

| | | | Amount | | |
|---|---|---|---|---|---|
| Step | Description | Mobile Phase | Column Volumes | Volume in mL | Time in minutes |
| 1 | Pre-Equilibration | 50 mM NaPi, 0.1M NaCl, pH 6.7 | 5.0 | 402.1 | 60 |
| 2 | Equilbration | 2 mM NaPi, dilute MES, 0.1M NaCl, pH 6.7 | 3.0 | 241.3 | 36 |

TABLE III-continued

Treatment Protocol for Simulated Cycles of Separation and Column Restoration

| Step | Description | Mobile Phase | Column Volumes | Volume in mL | Time in minutes |
|---|---|---|---|---|---|
| 3 | Sample | 2 mM NaPi, dilute MES, dilute Tris, 0.1M NaCl, pH 6.7 | 7.0 | 563.0 | 84 |
| 4 | Equipment line rinse | Ultra Pure Water, line flush | 0.08 | 6.4 | 1.0 |
| 5 | Wash | 2 mM NaPi, 0.1M NaCl, pH 6.7 | 3.0 | 241.3 | 36 |
| 6 | Gradient Elution | Gradient 8-90%, 2 mM NaPi, 0.1M NaCl, pH 6.7 → 50 mM NaPi, 0.1M NaCl, pH 6.7 | 10.0 | 804.2 | 120 |
| 7 | Resin clearance | 50 mM NaPi, 0.1M NaCl, pH 6.7 | 2.0 | 160.8 | 24 |
| 8 | Unbuffered In-Situ Restoration | 50 mM CaCl$_2$ | 3.0 | 241.3 | 36 |
| 9 | Wash | 2 mM NaPi, 0.1M NaCl, pH 6.7 | 0.1 | 8.0 | 1.2 |
| 10 | Regeneration | 400 mM NaPI, pH 7.0 | 2.0 | 160.8 | 24 |
| 11 | Sanitization | 1N NaOH | 2.0 | 160.8 | 24 |

In Table III, dilute MES refers to an MES concentration of at least about 10 mM, 15 mM, or 20 mM MES and less than about 25 mM or 30 mM MES. Dilute Tris refers to a Tris concentration of at least about 2 mM, 3 mM, 4 mM, 5 mM, 10 mM, or 15 mM Tris and less than about 20 mM, or 25 mM Tris.

As in Example 1, 25 cycles were performed with measurements of particle mass and particle strength taken before the first cycle and after the last cycle. The measurements indicate that particle mass for the entire column increased by 7.18% and particle strength decreased by 20%, over the course of the 25 cycles. Thus, although some regeneration was achieved, as evidenced by the increase in mass and the smaller loss of particle strength compared to Example 1, the apatite is still significantly degraded.

Example 3

This example illustrates the result of incorporating an in situ regeneration protocol that includes a buffered calcium regeneration solution. The experiment was performed on a column measuring 20 cm in length and 2.2 cm in internal diameter, with an internal volume of 76.03 mL, and the packing was ceramic hydroxyapatite Type I in 40-micron particles weighing approximately 48 grams, the resulting mobile phase flow rate through the column being 250 cm/h. A series of 25 consecutive cycles were performed, each cycle consisting of the following nine steps:

TABLE IV

Treatment Protocol

| Step | Description | Mobile Phase | Column Volumes | Volume in mL | Time in minutes |
|---|---|---|---|---|---|
| 1 | Rinse | Water | 1.0 | 76.0 | 4.8 |
| 2 | Pre-Equilibration | 400 mM NaPi, pH 7.0 | 3.0 | 228.1 | 14.4 |
| 3 | Equilibration | 5 mM NaPi, 5 mM MES, pH 6.5 | 6.0 | 456.2 | 28.8 |
| 4 | Elution | 10 mM NaPi, 25 mM MES, 1.0M NaCl, pH 6.5 | 6.0 | 456.2 | 28.8 |
| 5 | Buffered In-Situ Restoration | 50 mM CaCl2, 10 mM BES, pH 7.5 | 3.0 | 228.1 | 14.4 |
| 6 | Rinse | Water | 2.0 | 152.1 | 9.6 |
| 7 | Regeneration | 400 mM NaPi, pH 7.0 | 2.0 | 152.1 | 9.6 |
| 8 | Rinse | Water | 1.0 | 76.0 | 4.8 |
| 9 | Sanitization | 1N NaOH | 2.0 | 152.1 | 9.6 |

Hydroxyapatite obtained from a column operated for 25 cycles using the protocol in Table IV gained 4.74% in mass and increased 30% in particle strength compared to an unused hydroxyapatite control. These results demonstrate that the use of a buffered calcium solution, followed by application of a phosphate buffer and then a hydroxide provides a significant and surprising degree of regeneration, as evidenced by both an increase in mass and a significant increase in particle strength.

Example 4

This example illustrates the result of incorporating an in situ regeneration protocol that includes a buffered calcium regeneration solution into an apatite based purification protocol that utilizes alkali metal salt step gradient elution. The experiment was performed on a column measuring 20 cm in length and 2.2 cm in internal diameter, with an internal volume of 76.03 mL, and the packing was ceramic hydroxyapatite Type I in 40-micron particles weighing approximately 48 grams, the resulting mobile phase flow rate through the column being 400 cm/h. A series of 30 consecutive cycles were performed, each cycle consisting of the following eight steps:

TABLE V

Treatment Protocol

| Step | Description | Mobile Phase | Column Volumes | Volume in mL | Time in minutes |
|---|---|---|---|---|---|
| 1 | Pre-Equilibration | 400 mM NaPi, pH 7.0 | 3.0 | 228.1 | 9 |
| 2 | Equilibrium-Load-Wash | 10 mM NaPi, pH 6.5 | 10.0 | 760.3 | 30 |
| 3 | Elution | 10 mM NaPi, 1.0M NaCl, pH 6.5 | 6.0 | 456.2 | 18 |
| 4 | Rinse | 10 mM NaPi, pH 6.5 | 0.2 | 15.2 | 0.6 |
| 5 | Buffered In-Situ Restoration | 50 mM $CaCl_2 \cdot 2H_2O$, 100 mM MES, pH 7 | 3.0 | 228.1 | 9 |
| 6 | Rinse | 10 mM NaPi, pH 6.5 | 0.2 | 15.2 | 0.6 |
| 7 | Regeneration | 400 mM NaPi, pH 7.0 | 2.0 | 152.1 | 6 |
| 8 | Sanitization | 1N NaOH | 2.0 | 152.1 | 6 |

Hydroxyapatite obtained from a column operated for 30 cycles using the protocol in Table V gained 20.8% in mass and increased 13% in particle strength compared to an unused hydroxyapatite control. These results demonstrate that the use of a buffered calcium solution provides a significant and surprising degree of regeneration even when a high concentration of alkali metal salt is utilized in the elution step.

Example 5

This example illustrates the result of incorporating an in situ regeneration protocol that includes a buffered calcium regeneration solution into an apatite based purification protocol that utilizes alkali metal salt step gradient elution. The experiment was performed on a column measuring 20 cm in length and 1.6 cm in internal diameter, with an internal volume of 40.21 mL, and the packing was ceramic hydroxyapatite Type I in 40-micron particles weighing approximately 25 grams, the resulting mobile phase flow rate through the column being 400 cm/h. A series of 25 consecutive cycles were performed, each cycle consisting of the following eight steps:

TABLE VI

Treatment Protocol

| Step | Description | Mobile Phase | Column Volumes | Volume in mL | Time in minutes |
|---|---|---|---|---|---|
| 1 | Pre-Equilibration | 400 mM NaPi, pH 7.0 | 3.0 | 120.6 | 9 |
| 2 | Equilibrium-Load-Wash | 10 mM NaPi, pH 6.5 | 10.0 | 402.1 | 30 |
| 3 | Elution | 10 mM NaPi, 1.0M NaCl, pH 6.5 | 6.0 | 241.3 | 18 |
| 4 | Rinse | 10 mM NaPi, pH 6.5 | 0.2 | 8.0 | 0.6 |
| 5 | Buffered In-Situ Restoration | 50 mM $CaCl_2 \cdot 2H_2O$, 100 mM MES, pH 7 | 1.1 | 44.2 | 3.3 |
| 6 | Rinse | 10 mM NaPi, pH 6.5 | 0.2 | 8.0 | 0.6 |
| 7 | Regeneration | 400 mM NaPi, pH 7.0 | 2.0 | 80.4 | 6 |
| 8 | Sanitization | 1N NaOH | 2.0 | 80.4 | 6 |

Hydroxyapatite obtained from a column operated for 25 cycles using the protocol in Table VI gained 12.6% in mass and increased 12% in particle strength compared to an unused hydroxyapatite control. The results demonstrate that significant regeneration is achieved even when a high concentration of alkali metal salt is utilized in the elution step. Moreover, the substantial regeneration is achieved with a low volume (1.1 column volumes) of buffered calcium solution.

Example 6

This example illustrates the result of incorporating an in situ regeneration protocol that includes a buffered calcium regeneration solution into an alkali metal salt supplemented phosphate gradient based apatite based purification protocol. The experiment was performed on a column measuring 40 cm in length and 2.2 cm in internal diameter, with an internal volume of 152.05 mL, and the packing was ceramic hydroxyapatite Type I in 40-micron particles weighing approximately 96 grams, the resulting mobile phase flow rate through the column being 350 cm/h. A series of 30 consecutive cycles were performed, each cycle consisting of the following eleven steps:

TABLE VII

Treatment Protocol

| Step | Description | Mobile Phase | Column Volumes | Amount mL/min | Volume in mL | Time in minutes |
|---|---|---|---|---|---|---|
| 1 | Equilibration 1 | 50 mM NaPi, 0.1M NaCl, pH 6.7 | 1 | 11.09 | 152.1 | 13.7 |
| 2 | Equilibration 1 | 50 mM NaPi, 0.1M NaCl, pH 6.7 | 4 | 22.17 | 608.2 | 27.4 |
| 3 | Equilibration 2 | 2 mM NaPi, dilute MES, 0.1M NaCl, pH 6.7 | 3 | 22.17 | 456.2 | 20.6 |
| 4 | Sample | 2 mM NaPi, dilute MES, 0.1M NaCl, pH 6.7 | 7 | 22.17 | 1064.4 | 48 |
| 5 | Wash | 2 mM NaPi, 0.1M NaCl, pH 6.5 | 3 | 22.17 | 456.2 | 20.6 |
| 6 | Gradient | 10% Equil-1, 90% 0.1M NaCl → 90% Equil-1, 10% 0.1M NaCl | 10 | 22.17 | 1520.5 | 68.6 |
| 7 | Equilibration 1 | 50 mM NaPi, 0.1M NaCl, pH 6.7 | 2 | 22.17 | 304.1 | 13.7 |
| 8 | Equilibration 2 | 2 mM NaPi, dilute MES, 0.1M NaCl, pH 6.7 | 0.2 | 22.17 | 30.41 | 1.4 |
| 9 | In-Situ Restoration | 50 mM $CaCl_2$, 100 mM MES, pH 7.0 | 3 | 11.09 | 456.2 | 41.1 |
| 10 | Equilibration 2 | 2 mM NaPi, dilute MES, 0.1M NaCl, pH 6.7 | 0.2 | 11.09 | 30.41 | 2.7 |
| 11 | Regeneration | 400 mM NaPi, pH 7.0 | 2 | 11.09 | 304.1 | 27.4 |
| 12 | Sanitization | 1M NaOH | 2 | 11.09 | 304.1 | 27.4 |

In Table VII, dilute MES refers to an MES concentration of at least about 10 mM, 15 mM, or 20 mM MES and less than about 25 mM or 30 mM MES. Dilute Tris refers to a Tris concentration of at least about 2 mM, 3 mM, 4 mM, 5 mM, 10 mM, or 15 mM Tris and less than about 20 mM, or 25 mM Tris.

Hydroxyapatite obtained from a column operated for 30 cycles using the protocol in Table VII gained 18% in mass and increased 45% in particle strength compared to an unused hydroxyapatite control. Again, the protocol provides a significant and surprising degree of apatite regeneration as evidenced by a gain in both apatite mass and apatite particle strength.

Example 7

This example illustrates the result of incorporating an in situ regeneration protocol that includes a buffered calcium regeneration solution into a phosphate gradient based apatite based purification protocol. The experiment was performed on a column packed with 40-micron ceramic hydroxyapatite Type I particles, the resulting mobile phase flow rate through the column being 250 cm/h. A series of consecutive cycles were performed, each cycle consisting of the steps outlined in Table VIII.

TABLE VIII

Treatment Protocol

| Step | Protocol Reagent | Column Volumes |
|---|---|---|
| 1 | Equilibration 1 | 5.0 |
| 2 | Equilibration 2 | 3.0 |
| 3 | Sample | 7.0 |
| 4 | Wash | 3.0 |
| 5 | Gradient 10-90% 0.1M NaCl > 0.1M NaCl/phosphate solution | 10.0 |
| 6 | Wash | 2.0 |
| 7 | Line rinse | 0.4 |
| 8 | Calcium In-Situ Restoration solution | Varies |
| 9 | Line rinse | 0.4 |
| 10 | 400 mM NaPi, pH 7.0 | 2.0 |
| 11 | 1M NaOH | 2.0 |

The "Calcium ISR solution" listed in Table VIII was varied for each experiment as described in Table IX.

TABLE IX

Calcium ISR (in situ regeneration)

| Legend | dashed black | purple | orange | dashed orange | blue | dashed blue | light blue | dashed light blue | red |
|---|---|---|---|---|---|---|---|---|---|
| Experiment | 5897-072/Col17 | 5897-045 Baseline | 6141-034 | 6141-035 | 6141-037 | 6141-038 | 6141-040 | 6141-041 | 6045-023 |
| Cycles | 20 | 30 | 24 | 24 | 24 | 24 | 24 | 24 | 24 |
| [CaCl2] mM | 50.0 | | 10.0 | 25.0 | 25.0 | 25.0 | 5.74 | 10.2 | 50.0 |
| [MES] mM | | | 100 | 100 | 100 | 100 | 20 | | 100 |
| pH | | | 7.00 | 7.00 | 5.60 | 6.20 | 5.40 | 5.30 | 7.00 |
| CV | 3.00 | 0 | 1.10 | 1.10 | 1.10 | 1.10 | 3.00 | 3.00 | 1.10 |
| [PO4] mM | | | | | | | 23 | 23 | |

Table X provides further experimental details for a test of the relative selectivity of standard proteins on four lots of CHT Type 1, 40 μm control media.

TABLE X

Relative Selectivity Protocol

| | CV | |
|---|---|---|
| FR, cm/hr | 2.03 250 | |
| Column ID cm | Length | ml/min |
| 0.692 Area cm² 0.3761 | 5.4 | 1.57 |
| Protiens in DH2O | mg | 10 ml |
| Ovalbumin | 100 | |
| Myoglogin | 75 | |
| α-chymotrysinogen a | 70 | |
| Cytochrome C | 70 | |
| Step | Reagent | CV |
| Sanitize | 1N NaOH | 3.0 |
| Regen | 400 mM NaPi, pH 6.8 | 4.0 |
| Equil | 5 mM NaPi, pH 6.8 | 15.0 |
| Inject | Protein Load | 0.1 |
| Equil | 5 mM NaPi, pH 6.8 | 1.0 |
| Gradient | Gradient 0 –> 75 Regen | 15.0 |
| Regen | 400 mM NaPi, pH 6.8 | 3.0 |

Figure 2:
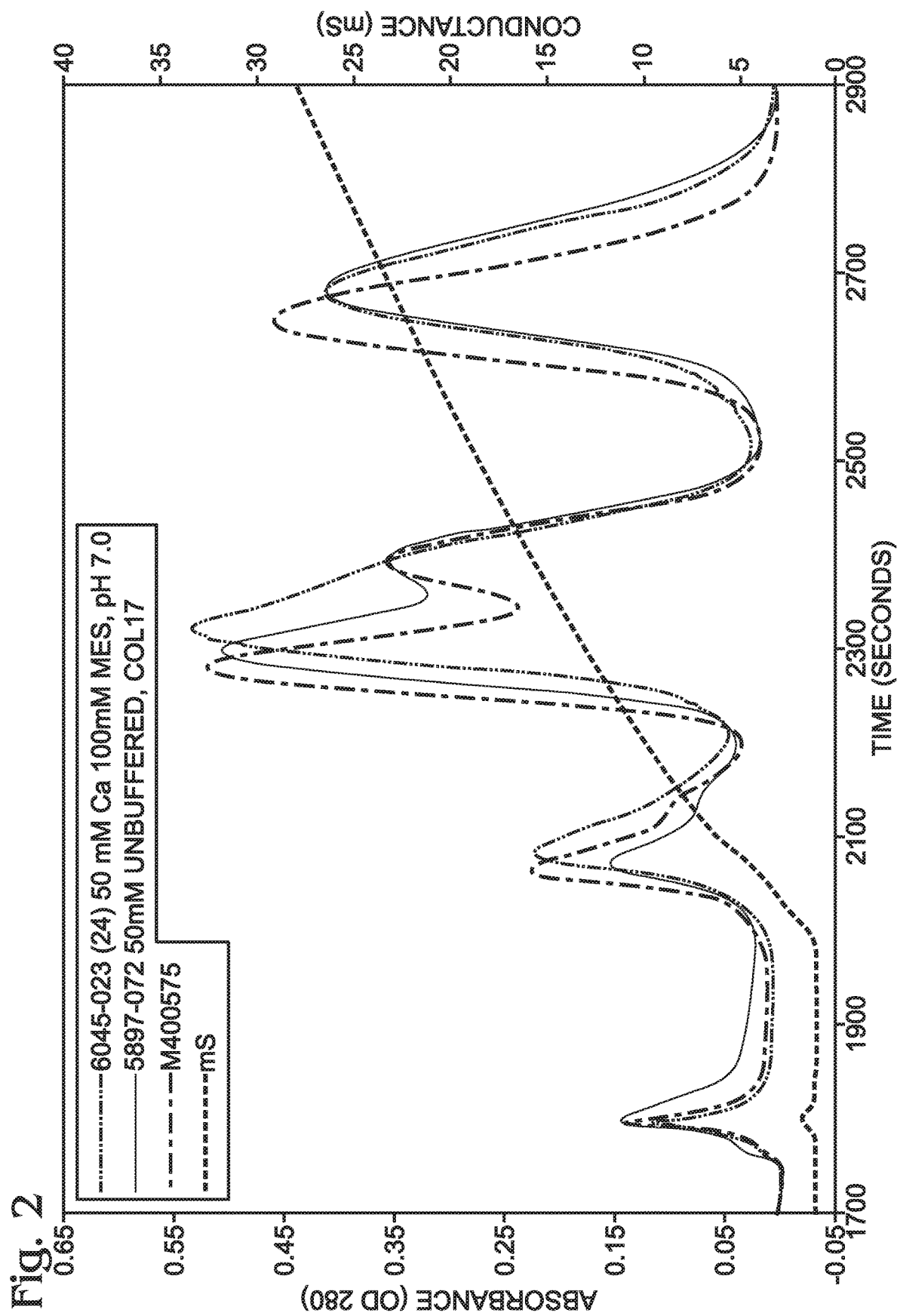
FIG. 2: depicts results from performing the purification profile of Example 7, Table X, after application of indicated in situ regeneration solutions.

Results from the performing the purification protocol of Table X are illustrated in FIG. 1. The apatite media was then cycled with a buffered regeneration solution containing 50 mM calcium and 100 mM MES, or an unbuffered calcium regeneration solution containing 50 mM calcium. The relative selectivity of alpha-chymotrypsinogen A changes on media cycled with 50 mM calcium buffered with 100 mM MES solution at pH 7.0 (red), as shown in FIG. 2. As also shown in FIG. 2, the selectivity is maintained after cycling with an unbuffered in situ regeneration (ISR) solution (black dotted) although a loss in resolution is noted relative to the control (green).

Figure 3:
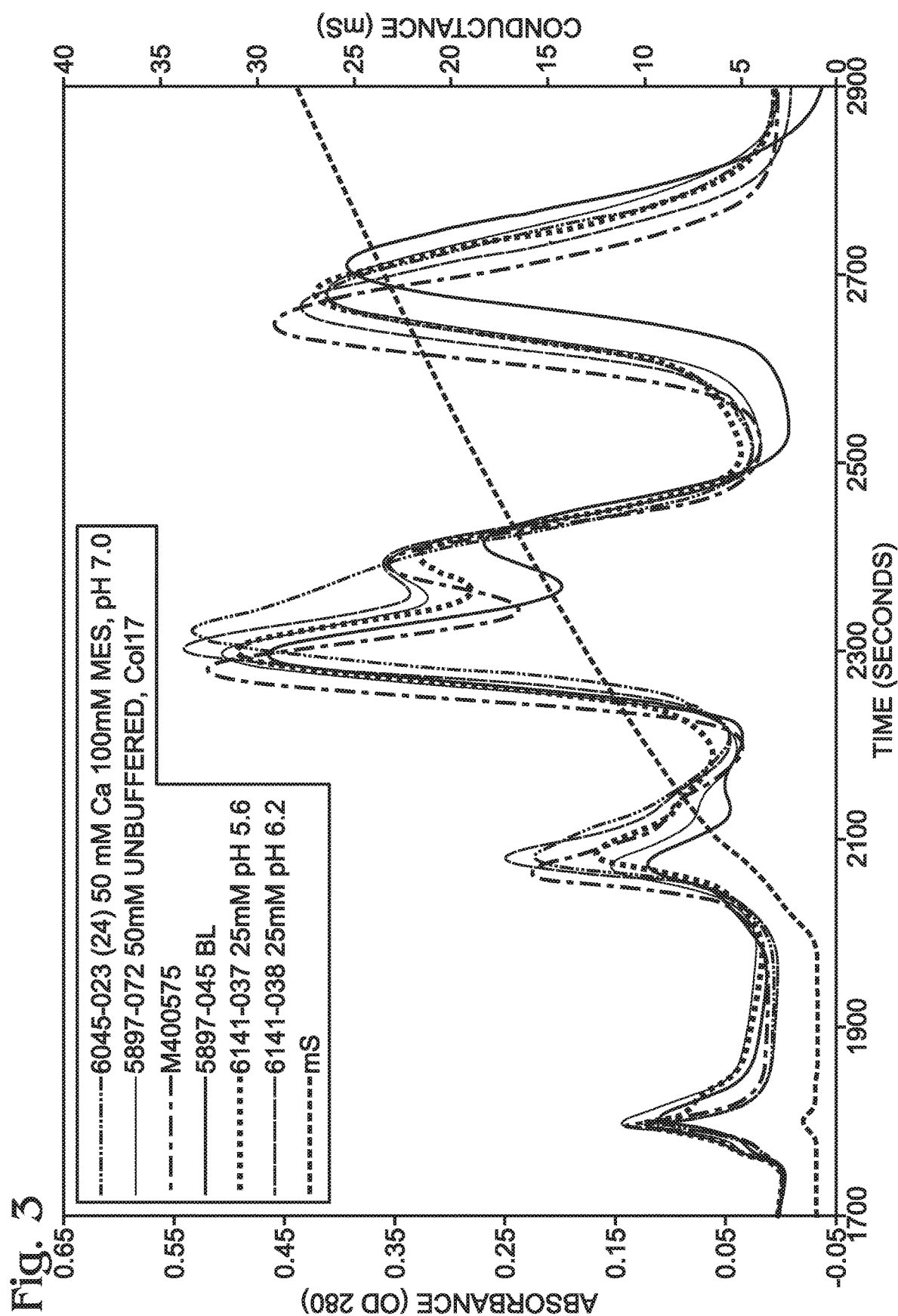
FIG. 3: depicts results from performing the purification profile of Example 7, Table X, after application of indicated in situ regeneration solutions.

FIG. 3 shows that the relative selectivity of alpha-chymotrypsinogen A is maintained when cycled with an the ISR solution of 25 mM calcium chloride buffered at pH 6.2 with 100 mM MES (dashed blue) or buffered at pH 5.6 (blue). The resolution between myoglobin and alpha-chymotrypsinogen A at pH 6.2 or 5.6 is affected but not their relative selectivity. Their relative selectivity is similar to the baseline protocol resin (5897-045 BL) absent the buffered ISR solution (purple), control resin (green) and unbuffered ISR resin (5897-072/Col17 (dashed black). The relative selectivity of resin cycled with an ISR solution that is 50 mM calcium buffered at pH 7.0 with 100 mM MES (red) is lost.

Figure 4:
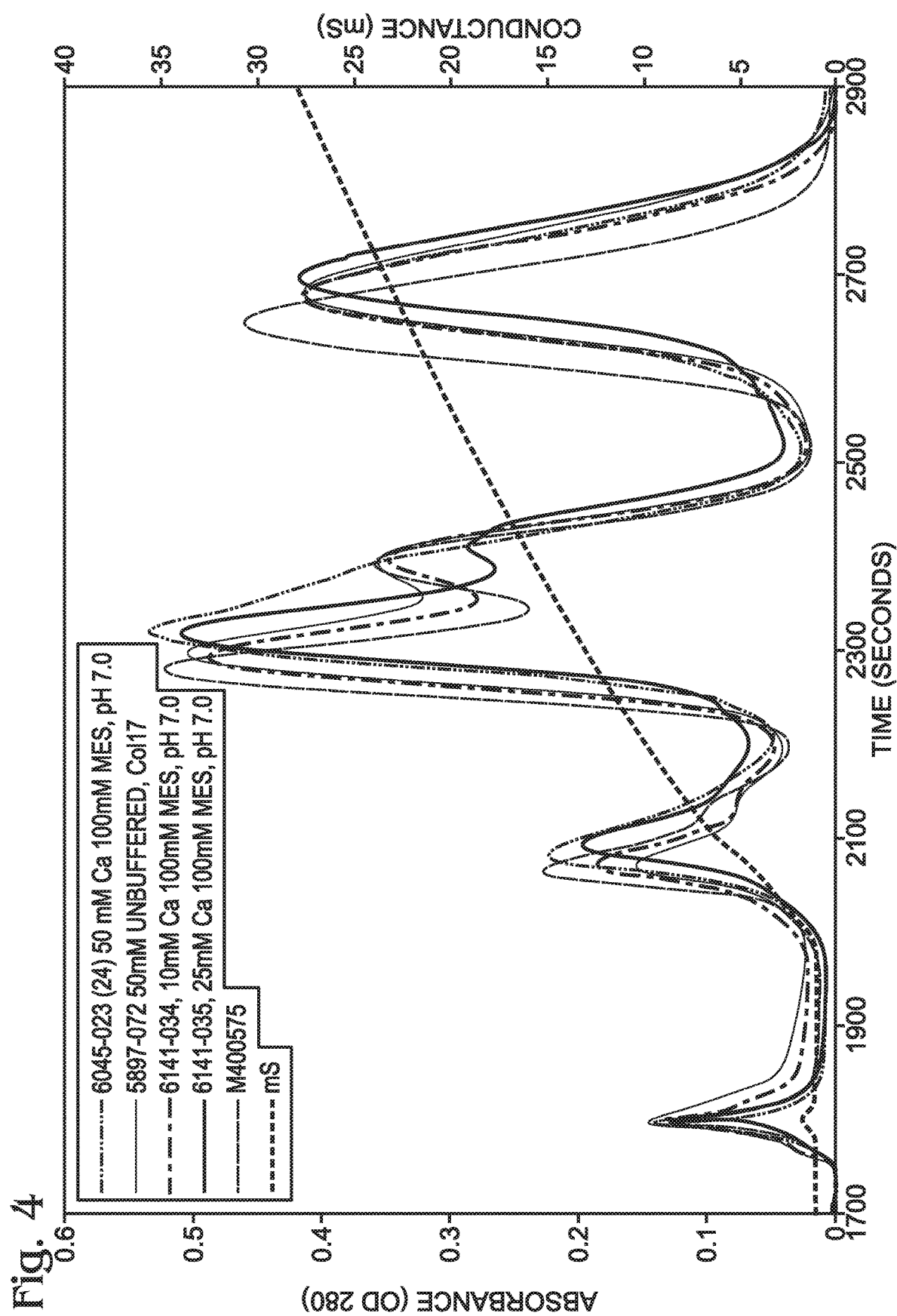
FIG. 4: depicts results from performing the purification profile of Example 7, Table X, after application of indicated in situ regeneration solutions.

FIG. 4 shows that the relative selectivity of alpha-chymotrypsinogen A is maintained similarly to the control (green) when the concentration of calcium in the buffered ISR solution during cycling is reduced to 10 mM (orange) or 25 mM (light blue) while maintaining the buffer at pH 7.0 with 100 mM MES. This is not the case for the 50 mM calcium solution under the same buffering conditions (red). The resolution between myoglobin and alpha-chymotrypsinogen A is reduced to that observed with unbuffered ISR (dotted black) but the selectivity for each is maintained.

Figure 5:
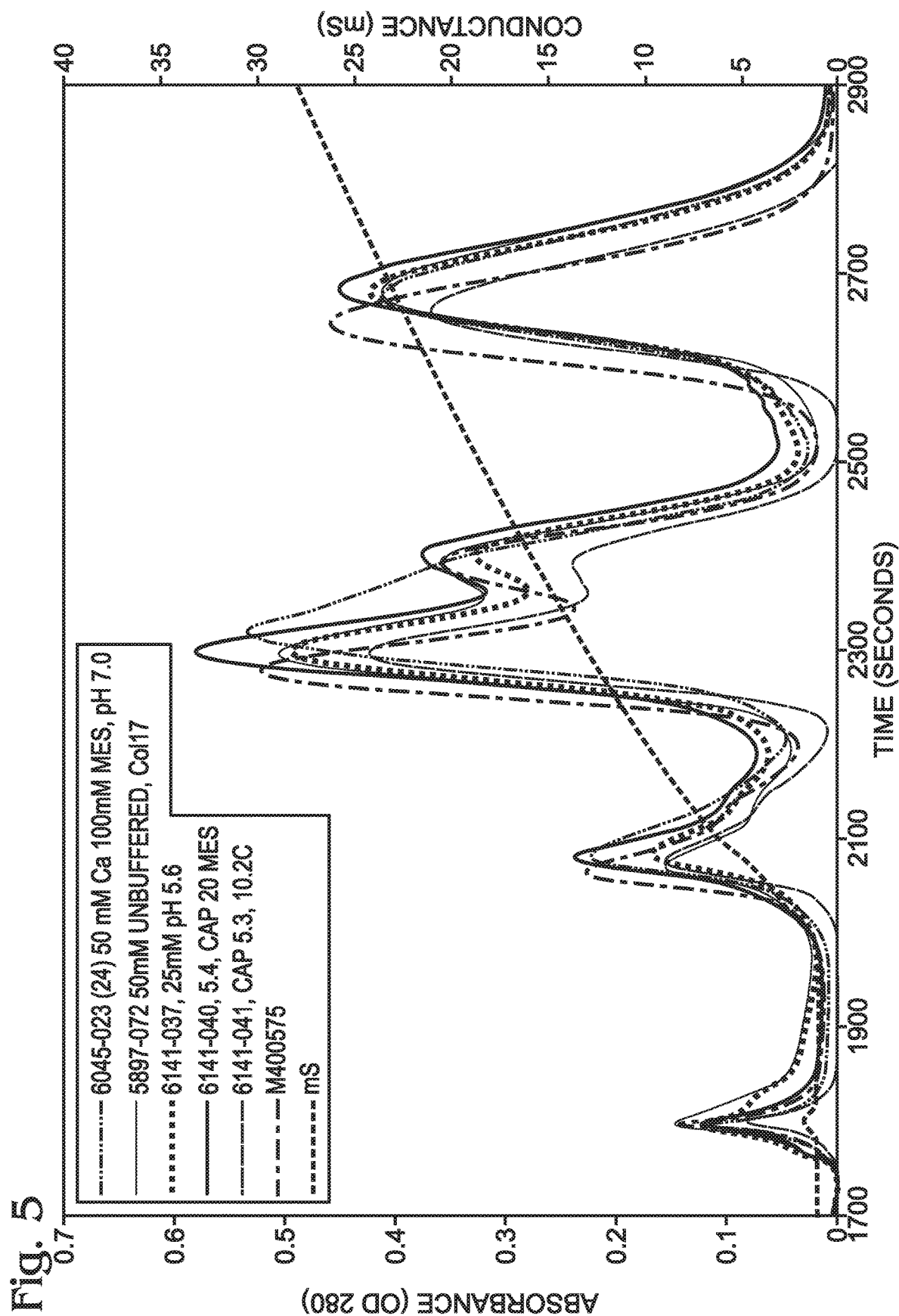
FIG. 5: depicts results from performing the purification profile of Example 7, Table X, after application of indicated in situ regeneration solutions.

FIG. 5 shows that the relative selectivity is unaffected by cycling with a regeneration solution containing a low concentration of calcium (5.74 mM) buffered at pH 5.40 with 20 mM MES or 23 mM phosphate (light blue). In addition 10.2 mM calcium containing 23 mM phosphate maintains selectivity but has decreased resolution (dashed light blue). Both of these conditions are comparable to 25 mM calcium buffered at pH 5.6 with 100 mM MES (blue) and unbuffered ISR (dashed black).

The mass of the apatite media increased for all cycling experiments conducted with in situ regeneration (ISR), as depicted in Table XI. The baseline media (5897-045 BL) decreased in mass. With exception of experiment 5897-017/Col17 the loss in media strength did not decline below the value in N/mm for the other experiments.

TABLE XI

Results

| | Experiment | | | | | | | |
|---|---|---|---|---|---|---|---|---|
| | 5897-072/Col17 | 5897-045 Baseline | 6141-034 | 6141-035 | 6141-037 | 6141-038 | 6141-040 | 6141-041 |
| Cycles | 20 | 30 | 24 | 24 | 24 | 24 | 24 | 24 |
| Mass change | 3.92 | −2.64 | 0.14 | 0.96 | 0.50 | 1.03 | 0.35 | 0.57 |
| % Change | 4.09 | −2.76 | 1.10 | 7.58 | 3.95 | 8.13 | 2.76 | 4.50 |
| Media Strength | | | | | | | | |
| Average | 4.90 | 4.03 | 3.41 | 2.78 | 2.90 | 2.77 | 3.48 | 2.74 |
| STDEV | 0.582 | 0.235 | 0.186 | 0.230 | 0.103 | 0.101 | 0.240 | 0.250 |
| RSD | 0.119 | 0.058 | 0.054 | 0.083 | 0.035 | 0.037 | 0.069 | 0.091 |
| N/mm | 20.4 | 24.8 | 29.4 | 36.0 | 34.4 | 36.1 | 28.8 | 36.5 |

The results indicate that both the calcium concentration and the pH of buffered calcium solution affect the relative selectivity of standard proteins. Acceptable performance can be achieved with a buffered calcium solution at, e.g., a pH of at least about 5.3, a calcium concentration of at least about 5 mM and a phosphate or zwitterionic buffer concentration of between about 20 mM and 100 mM.

All patents, patent applications, and other published reference materials cited in this specification are hereby incorporated herein by reference in their entirety.

What is claimed is:

1. A method of purifying a target analyte with an apatite solid surface, the method comprising:
  (a) contacting the apatite solid surface with the target analyte, thereby separating the target analyte from one or more contaminants;

(b) collecting the target analyte, wherein the contacting, the collecting, or both cause deterioration of resin mass or particle strength; and (c) after the collecting and before subsequent loading of additional target analyte, regenerating the apatite solid surface, the regenerating comprising:

(i) contacting the apatite solid surface with a buffered calcium solution comprising a calcium ion at a concentration of at least 5 mM and a zwitterionic buffer, wherein the ratio of zwitterionic buffer concentration to calcium ion concentration is at least 2, and the pH of the buffered calcium solution is at least 5;

(ii) after (i), contacting the apatite solid surface with a phosphate buffered solution at a pH of at least 6.5; and (iii) after (ii), contacting the apatite solid surface with a solution comprising an hydroxide, wherein step (c) reduces, eliminates, or reverses the deterioration of the resin mass or particle strength of said apatite solid surface.

2. The method of claim 1, wherein (a) comprises binding the target analyte to the apatite solid surface, and (b) comprises eluting the target analyte from the apatite solid surface.

3. The method of claim 1, wherein (a) comprises contacting the apatite solid surface with the target analyte, thereby flowing the target analyte through the apatite solid surface, and (b) comprises collecting the target analyte in the flow through.

4. The method of claim 1, wherein the zwitterionic buffer is a sulfonic acid containing buffer.

5. The method of claim 4, wherein the sulfonic acid containing buffer is MES, PIPES, ACES, MOPSO, MOPS, BES, TES, HEPES, DIPSO, TAPS, TAPSO, POPSO, HEPPSO, EPPS, CAPS, CAPSO, or CHES.

6. The method of claim 5, wherein the sulfonic acid containing buffer is MES.

7. The method of claim 1, wherein the calcium ion concentration is less than 50 mM.

8. The method of claim 1, wherein the calcium ion concentration is at least 25 mM.

9. The method of claim 1, wherein the ratio of zwitterionic buffer concentration to calcium ion concentration is at least 2.5.

10. The method of claim 1, wherein the buffered calcium solution comprises calcium chloride or calcium nitrate.

11. The method of claim 1, wherein the buffered calcium solution is at a pH of at least 5.3.

12. The method of claim 1, wherein the buffered calcium solution is at a pH of between 5.3 and 7.

13. The method of claim 1, wherein the phosphate buffered solution comprises a solution containing from 0.1 M to 1.0 M phosphate at a pH of from 6.5 to 8.

14. The method of claim 13, wherein the phosphate buffered solution comprises 400 mM phosphate at a pH of 7.0.

15. The method of claim 1, wherein the hydroxide comprises an alkaline hydroxide.

16. The method of claim 15, wherein the alkaline hydroxide comprises sodium or potassium hydroxide.

17. The method of claim 1, wherein the regenerating reverses or eliminates degradation of the column that occurs during protein purification or column cleaning steps.

18. The method of claim 1, wherein the contacting of the apatite solid surface with the phosphate buffered solution comprising phosphate at a pH of at least 6.5 further comprises:

contacting the apatite solid surface with a solution comprising phosphate at a concentration of 10 mM or less at a pH of at least 6.5; and then contacting the apatite solid surface with a solution comprising phosphate at a concentration of at least 100 mM at a pH of at least 6.5.

19. The method of claim 1, wherein the regenerating consists of step (c)(i), followed by contacting the apatite with a wash, then steps (c)(ii) and, then (c)(iii).

* * * * *